US00PP22367P2

(12) United States Plant Patent
Podaras

(10) Patent No.: US PP22,367 P2
(45) Date of Patent: Dec. 20, 2011

(54) ***BUDDLEJA* PLANT NAMED 'PODARAS #14'**

(50) Latin Name: *(Buddleja davidii×Buddleja alternifolia)×Buddleja davidii*
Varietal Denomination: Podaras #14

(75) Inventor: Peter Podaras, Ithaca, NY (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 12/660,670

(22) Filed: Mar. 2, 2010

(51) Int. Cl.
*A01H 5/00* (2006.01)

(52) U.S. Cl. ..... Plt./242

(58) Field of Classification Search ..... Plt./242
See application file for complete search history.

(56) References Cited

U.S. PATENT DOCUMENTS

PP14,370 P2 * 12/2003 Turrell et al. ..... Plt./242
* cited by examiner

*Primary Examiner* — Susan McCormick Ewoldt
(74) *Attorney, Agent, or Firm* — C. A. Whealy

(57) ABSTRACT

A new and distinct cultivar of *Buddleja* plant named 'Podaras #14', characterized by its compact, upright to outwardly spreading plant habit; freely flowering habit; sterile violet-colored flowers with white-colored centers and greyed orange-colored throats; and good garden performance.

1 Drawing Sheet

Botanical designation: (*Buddleja davidii*×*Buddleja alternifolia*)×*Buddleja davidii.*

Cultivar denomination: 'PODARAS #14'.

BACKGROUND OF THE INVENTION

The present invention relates to a new and distinct cultivar of *Buddleja* plant, botanically known as (*Buddleja davidii*× *Buddleja alternifolia*)×*Buddleja davidii* and hereinafter referred to by the name 'Podaras #14'.

The new *Buddleja* plant is a product of a planned breeding program conducted by the Inventor in Ithaca, N.Y. The objective of the breeding program was to create new compact and sterile *Buddleja* plants with unique and attractive flower coloration.

The new *Buddleja* plant originated from a cross-pollination on Nov. 22, 2006 in Ithaca, N.Y., of an unnamed selection of *Buddleja davidii*×*Buddleja alternifolia*, not patented, as the female, or seed, parent with an unnamed selection of *Buddleja davidii*, not patented, as the male, or pollen, parent. The new *Buddleja* plant was discovered and selected by the Inventor as a single flowering plant within the progeny of the stated cross-pollination in a controlled environment in Ithaca, N.Y. in August, 2007.

Asexual reproduction of the new *Buddleja* plant by cuttings in a controlled greenhouse environment in West Chicago, Ill. since February, 2008, has shown that the unique features of this new *Buddleja* plant are stable and reproduced true to type in successive generations.

SUMMARY OF THE INVENTION

Plants of the new *Buddleja* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Podaras #14'.

These characteristics in combination distinguish 'Podaras #14' as a new and distinct *Buddleja* plant:

1. Compact, upright to outwardly spreading plant habit.
2. Freely flowering habit.
3. Sterile violet-colored flowers with white-colored centers and greyed orange-colored throats.
4. Good garden performance.

Plants of the new *Buddleja* differ from plants of the female parent selection in the following characteristics:

1. Plants of the new *Buddleja* are more upright and uniform than plants of the female parent selection.
2. Plants of the new *Buddleja* and the female parent selection differ in flower color as plants of the female parent selection have light mauve-colored flowers.

Plants of the new *Buddleja* differ from plants of the male parent selection in the following characteristics:

1. Plants of the new *Buddleja* are more vigorous and larger than plants of the male parent selection.
2. Plants of the new *Buddleja* and the male parent selection differ in flower color as plants of the male parent selection have dark purple-colored flowers with white-colored centers and orange-colored throats.

Plants of the new *Buddleja* can be compared to plants of *Buddleja davidii* 'Attraction', not patented. In side-by-side comparisons, plants of the new *Buddleja* and 'Attraction' differed in the following characteristics:

1. Plants of the new *Buddleja* were shorter and more compact than plants of 'Attraction'.
2. Plants of the new *Buddleja* and 'Attraction' differed in flower color as plants of 'Attraction' had red purple-colored flowers.

BRIEF DESCRIPTION OF THE PHOTOGRAPHS

The accompanying colored photographs illustrate the overall appearance of the new *Buddleja* plant, showing the colors as true as it is reasonably possible to obtain in colored reproductions of this type. Colors in the photographs may differ slightly from the color values cited in the detailed botanical description which accurately describe the colors of the new *Buddleja* plant.

The photograph at the bottom of the sheet comprises a side perspective view of a typical flowering plant of 'Podaras #14' grown in a container.

The photograph at the top of the sheet is a close-up view of a typical inflorescence of 'Podaras #14'.

DETAILED BOTANICAL DESCRIPTION

The aforementioned photographs and following observations, measurements and values describe plants grown in Abbotsford, British Columbia, Canada under commercial practice during the summer in one-gallon containers in an outdoor nursery. Plants were one year old when the photographs and description were taken. In the following description, color references are made to The Royal Horticultural Society Colour Chart, 2007 Edition, except where general terms of ordinary dictionary significance are used.

Botanical classification: (*Buddleja davidii*×*Buddleja alternifolia*)×*Buddleja davidii* 'Podaras #14'.

Parentage:

*Female, or seed, parent.*—Unnamed selection of *Buddleja davidii*×*Buddleja alternifolia*, not patented.

*Male, or pollen, parent.*—Unnamed selection of *Buddleja davidii*, not patented.

Propagation:

*Type.*—By cuttings.

*Time to initiate roots plant, summer.*—About two weeks at temperatures of 18° C. to 24° C.

*Time to initiate roots plant, winter.*—About two to three weeks at temperatures of 18° C. to 24° C.

*Time to produce a rooted plant, summer.*—About three weeks at temperatures of 18° C. to 24° C.

*Time to produce a rooted plant, winter.*—About three to four weeks at temperatures of 18° C. to 24° C.

*Root description.*—Fibrous, fine; white in color.

*Rooting habit.*—Freely branching; moderately dense.

Plant description:

*Plant form/habit.*—Deciduous perennial shrub; compact, upright and somewhat outwardly spreading habit; broad inverted triangle; moderately vigorous growth habit.

*Plant height.*—About 40 cm.

*Plant width (spread).*—About 28 cm by 32 cm.

*Lateral branches.*—Quantity: About nine main branches per plant. Length: About 30 cm. Diameter: About 4 mm. Internode length: About 4.8 cm. Strength: Moderately strong. Texture, developing stems: Pubescent. Texture, mature stems: Smooth, glabrous. Color, developing: Close to 194B. Color, mature: Close to 187A.

Foliage description:

*Arrangement.*—Opposite, simple.

*Length.*—About 7 cm.

*Width.*—About 2.3 cm.

*Shape.*—Elliptical.

*Apex.*—Acute.

*Base.*—Attenuate.

*Margin.*—Serrulate.

*Texture, upper surface.*—Slightly pubescent.

*Texture, lower surface.*—Lanulose.

*Venation pattern.*—Pinnate, reticulate.

*Color.*—Developing leaves, upper surface: Close to 137A. Developing leaves, lower surface: Close to 194A. Fully expanded leaves, upper surface: Darker than 147A; venation, close to 147A. Fully expanded leaves, lower surface: Close to 194A; venation, close to 147C.

*Petiole.*—Length: About 5 mm. Diameter: About 1.5 mm. Texture, upper and lower surfaces: Lanulose. Color, upper surface: Close to 146B. Color, lower surface: Close to 146C.

Flower description:

*Flower type/habit.*—Single rotate and salverform flowers arranged in compound terminal and axillary panicles; flowers face upright and outward; panicles roughly conical in shape; freely flowering habit with about 344 flower buds and flowers developing per inflorescence.

*Fragrance.*—Faint, sweet.

*Natural flowering season.*—Plants begin flowering about three months after planting; flowering continuous from spring until frost.

*Postproduction longevity.*—Flowers last about five to seven days on the plant; flowers persistent.

*Flower buds.*—Height: About 1.2 cm. Diameter: About 2.5 mm. Shape: Oblong. Color: Close to N92D.

*Inflorescence height.*—About 7.2 cm.

*Inflorescence diameter.*—About 4.4 cm.

*Flower diameter.*—About 7 mm to 9 mm.

*Flower depth.*—About 1.3 cm.

*Flower throat, diameter.*—About 2 mm.

*Flower tube, length.*—About 1 cm.

*Flower tube, diameter at base.*—About 1.5 mm.

*Petals.*—Quantity per flower: Typically four in a single whorl; petals fused into a narrow tube. Lobe length: About 4 mm. Lobe width: About 3 mm. Lobe shape: Roughly spatulate. Lobe apex: Rounded. Lobe margin: Erosulate. Texture, upper and lower lobe surfaces: Smooth, glabrous. Texture, throat: Slightly pubescent. Texture, tube: Smooth, glabrous. Color: Developing petals, upper surface: Close to 85A. Developing petals, lower surface: Close to 86C. Fully expanded petals, upper surface: Close to N87C; towards the base, close to NN155D; venation, close to N87C. Fully expanded petals, lower surface: Close to 94C to 94D; venation, close to 83B. Throat: Close to N170C; venation, close to N170C. Tube: Close to 165D; venation, close to 165D.

*Sepals.*—Quantity per flower: Typically four in a single whorl, fused towards the base; campanulate calyx. Length: About 1 mm. Width: About 1 mm. Shape: Lanceolate. Apex: Acute. Margin: Entire. Texture, upper surface: Smooth, glabrous. Texture, lower surface: Pubescent. Color, upper surface: Close to 146C. Color, lower surface: Close to 146A; towards the apex, tinted with close to N92D.

*Peduncles.*—Length: About 1.6 cm. Diameter: About 1.5 mm. Angle: Erect to about 45° from vertical. Strength: Strong. Texture: Lanulose. Color: Close to 194A.

*Pedicels.*—Length: About 2 mm. Diameter: About 1 mm. Angle: About 30° to 45° from peduncle axis. Strength: Moderately strong. Texture: Pubescent. Color: Close to 194B.

*Reproductive organs.*—Stamens: Quantity per flower: Typically four; filaments adnate to the corolla tube.

Filament length: About 4 mm. Filament color: Close to 160A. Anther shape: Lanceolate. Anther length: About 1 mm. Anther color: Close to 158A. Pollen amount: None. Pistils: Quantity per flower: One. Pistil length: About 3.5 mm. Stigma shape: Oval. Stigma color: Close to N144A. Style length: About 1 mm. Style color: Close to 145C. Ovary color: Close to 145A.

*Seed/fruit.*—Flowers of plants of the new *Buddleja* are sterile and seed and fruit development have not been observed.

Disease/pest resistance: Plants of the new *Buddleja* have been not been observed to be resistant to pathogens and pests common to *Buddleja.*

Garden performance: Plants of the new *Buddleja* have been observed to have good garden performance and tolerate rain, wind and temperatures ranging from about 0° C. to about 40° C.

It is claimed:

1. A new and distinct *Buddleja* plant named 'Podaras #14' as illustrated and described.

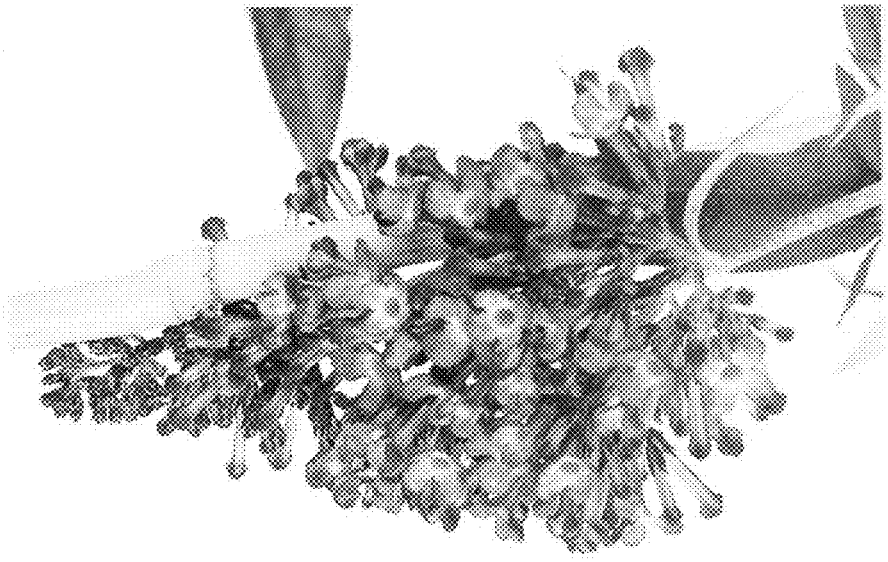
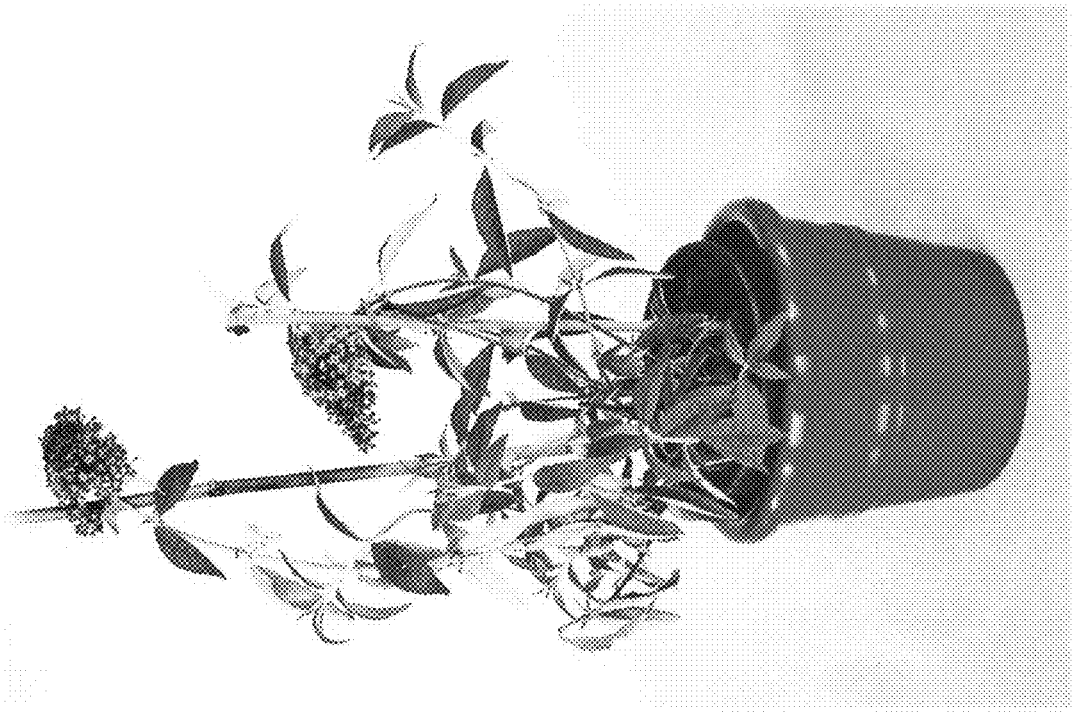

* * * * *